US010418495B2

(12) United States Patent
Park et al.

(10) Patent No.: US 10,418,495 B2
(45) Date of Patent: Sep. 17, 2019

(54) GALLIUM NITRIDE-BASED SENSOR HAVING HEATER STRUCTURE AND METHOD OF MANUFACTURING THE SAME

(71) Applicant: KOREA ADVANCED NANO FAB CENTER, Gyeonggi-do (KR)

(72) Inventors: Kyungho Park, Gyeonggi-do (KR); Chuyoung Cho, Gyeonggi-do (KR); Hyeong Ho Park, Daejeon (KR); Yu Min Koh, Gyeonggi-do (KR)

(73) Assignee: KOREA ADVANCED NANO FAB CENTER (KR)

( * ) Notice: Subject to any disclaimer, the term of this patent is extended or adjusted under 35 U.S.C. 154(b) by 0 days.

(21) Appl. No.: 16/130,721

(22) Filed: Sep. 13, 2018

(65) Prior Publication Data

US 2019/0097067 A1    Mar. 28, 2019

(30) Foreign Application Priority Data

Sep. 26, 2017   (KR) .................. 10-2017-0124251

(51) Int. Cl.
*H01L 31/02*   (2006.01)
*H01L 31/18*   (2006.01)
(Continued)

(52) U.S. Cl.
CPC ..... *H01L 31/02024* (2013.01); *G01N 27/124* (2013.01); *G01N 27/128* (2013.01);
(Continued)

(58) Field of Classification Search
CPC .................. H01L 29/66431; H01L 29/778
(Continued)

(56) References Cited

U.S. PATENT DOCUMENTS 9,038,437 B2 *   5/2015   Offermans ......... G01N 33/0009
                                                        73/31.06
2007/0018198 A1 *  1/2007  Brandes ............ H01L 29/66462
                                                        257/183
(Continued)

*Primary Examiner* — David Vu
*Assistant Examiner* — Brandon C Fox
(74) *Attorney, Agent, or Firm* — Mendelsohn Dunleavy, P.C.

(57) ABSTRACT

A gallium nitride-based sensor having a heater structure and a method of manufacturing the same are disclosed, the method including growing an n-type or p-type GaN layer on a substrate, growing a barrier layer on the n-type or p-type GaN layer, sequentially growing a u-GaN layer and a layer selected from among an $Al_xGa_{1-x}N$ layer, an $In_xAl_{1-x}N$ layer and an $In_xAl_yGa_{1-x-y}N$ layer on the barrier layer, patterning the n-type or p-type GaN layer to form an electrode, forming the electrode along the pattern formed on the n-type or p-type GaN layer, and forming a sensing material layer on the layer selected from among the $Al_xGa_{1-x}N$ layer, the $In_xAl_{1-x}N$ layer and the $In_xAl_yGa_{1-x-y}N$ layer, wherein a HEMT sensor or a Schottky diode sensor can be heated using an n-GaN (or p-GaN) layer, thus increasing the sensitivity of the sensor and reducing the restoration time.

25 Claims, 8 Drawing Sheets

(51) Int. Cl.
*H01L 29/778* (2006.01)
*H01L 29/66* (2006.01)
*G01N 27/12* (2006.01)
*G01N 27/414* (2006.01)
*G01N 33/00* (2006.01)
*H01L 31/0224* (2006.01)
*H01L 31/0304* (2006.01)

(52) U.S. Cl.
CPC ....... *G01N 27/4141* (2013.01); *G01N 33/005* (2013.01); *H01L 29/66431* (2013.01); *H01L 29/778* (2013.01); *H01L 31/0224* (2013.01); *H01L 31/03046* (2013.01); *H01L 31/1852* (2013.01); *G01N 27/129* (2013.01)

(58) Field of Classification Search
USPC .......................................................... 257/194
See application file for complete search history.

(56) References Cited

U.S. PATENT DOCUMENTS

2011/0068372 A1* 3/2011 Ren ...................... G01N 27/414
257/194
2013/0288378 A1* 10/2013 Gu ..................... G01N 27/4141
436/37
2018/0128774 A1* 5/2018 Kashyap ................ G01N 27/02

* cited by examiner

GALLIUM NITRIDE-BASED SENSOR HAVING HEATER STRUCTURE AND METHOD OF MANUFACTURING THE SAME

STATEMENT OF GOVERNMENTAL SUPPORT

This invention was made with government support under Project No. 2015M3A7B7044548 awarded by Nano Material Technology Development Program through the National Research Foundation of Korea (NRF) funded by the Ministry of Science, ICT and Future Planning. The government support was made at a contribution rate of 1/1 for the research period of Oct. 1, 2015 through Jun. 30, 2020. The supervising institute was the KOREA ADVANCED NANO FAB CENTER.

BACKGROUND OF THE INVENTION

Field of the Invention

The present invention relates to the manufacture of a gallium nitride-based sensor, and more particularly to a gallium nitride-based sensor having a heater structure and a method of manufacturing the same.

Description of the Related Art

Gallium nitride (GaN) has a high energy bandgap of 3.4 eV and an intrinsic carrier concentration of $10^{-10}$ $cm^{-3}$ at room temperature and thus retains high durability and enables the stable operation of devices even under conditions of high temperatures of 600° C. or more, high pressure and electromagnetic waves, compared to silicon and oxide semiconductors.

Also, GaN, having large lattice energy and a chemically stable structure, may exhibit outstanding chemical stability under conditions of strong acids and bases and high humidity compared to oxide semiconductors in the form of a thin film or a nanostructure.

In particular, an AlGaN/GaN HEMT (High Electron Mobility Transistor), configured such that an AlGaN thin film is grown on GaN, is able to form a 2-DEG (2-Dimensional Electron Gas) layer having very fast electron mobility at the interface of AlGaN and GaN through spontaneous polarization and piezoelectric effects due to mismatch of lattice constants, in which the 2-DEG layer exhibits a current change that is very sensitive to changes in charge quantity on a semiconductor surface, making it possible to manufacture a stable sensor, having a very small size, low power, fast response speed, and high sensitivity, using the same.

FIGS. 1A to 1C illustrate changes in the sensitivity of a hydrogen sensor depending on the temperature.

FIGS. 1A, 1B and 1C show changes in the sensitivity of a hydrogen sensor at different temperatures. With reference to FIGS. 1A, 1B and 1C, as the temperature is increased from room temperature to 100° C. and 500° C., the sensitivity of the hydrogen sensor can be seen to increase.

Specifically, in the case of a gas sensor or a chemical sensor, which is reusable using a sensing material, it is very important to reduce the reaction time required to detect a detection target material using a sensing material and the restoration time required to restore the sensor to the original state thereof after removal of the detection target material.

With the goal of reducing the reaction time (sensitivity) and the restoration time, heat may be applied from the outside to decrease the reaction time of the sensing material and the detection target material.

However, a gallium nitride-based sensor using a high-temperature epitaxy process makes it difficult to manufacture a heater for supplying heat to the sensing material.

Conventional techniques are a process of growing no epitaxial thin film, in which, for instance, a gas sensor manufactured on a Si substrate is obtained by first forming a micro heater (Pt, etc.) on a membrane structure, forming a sensor structure thereon, and performing backside silicon etching.

Since a GaN-based sensor is problematic in that an epitaxial thin film cannot be grown after the first formation of a heater (GaN-based epitaxy growth temperature is 1,000° C. or more), a sensor structure is formed using an epitaxial thin film already grown at high temperatures and a heater structure is formed on the sensor structure. In this case, however, the distance from the heater region to the sensing material is long and thus a large amount of power is consumed in order to control the temperature and the sensor area has to include the heater region, undesirably enlarging the size of the sensor.

Although the manufacture of a physical sensor, a chemical sensor, a biosensor, etc. using a GaN-based thin film requires the temperature of the sensor device to be controlled, it is difficult to manufacture a heater having low power consumption owing to the high heat capacity of the substrate having the GaN-based thin film grown thereon.

Moreover, it is not easy to perform a process of removing a portion of the substrate having the GaN-based thin film grown thereon in order to reduce the heat capacity of the region for manufacturing the sensor, making it difficult to manufacture a gallium nitride-based sensor having a heater.

SUMMARY OF THE INVENTION

Accordingly, the present invention has been made keeping in mind the above problems encountered in the related art, and the present invention is intended to provide a method of manufacturing a gallium nitride-based sensor having a heater structure.

In addition, the present invention is intended to provide a gallium nitride-based sensor having a heater structure.

Therefore, the present invention provides a method of manufacturing a gallium nitride-based sensor having a heater structure, comprising growing an n-type or p-type GaN layer on a substrate, growing a GaN ($Al_xGa_{1-x}N$, $In_xAl_{1-x}N$, or high-resistance GaN)-based monolayered or multilayered barrier layer on the n-type or p-type GaN layer, sequentially growing a u-GaN layer and a layer selected from the group consisting of an $Al_xGa_{1-x}N$ layer, an $In_xAl_{1-x}N$ layer and an $In_xAl_yGa_{1-x-y}N$ layer on the barrier layer, patterning the n-type or p-type GaN layer so as to form an electrode, forming the electrode along the pattern formed on the n-type or p-type GaN layer, and forming a sensing material layer on the layer selected from the group consisting of the $Al_xGa_{1-x}N$ layer, the $In_xAl_{1-x}N$ layer and the $In_xAl_yGa_{1-x-y}N$ layer.

Here, the n-type or p-type GaN layer may function as a heater for generating heat due to the current applied to the electrode. Also, the threshold voltage of the sensor device may be adjusted by changing the applied voltage.

Here, the barrier layer may be provided in the form of any one layer or a combination of layers selected from among an $Al_xGa_{1-x}N$ layer, an $In_xAl_{1-x}N$ layer and a high-resistance GaN layer.

Here, the barrier layer may function to prevent the current flowing in the n-type or p-type GaN layer from flowing to the sensor structure on the barrier layer.

Here, the forming the sensing material layer on the layer selected from the group consisting of the $Al_xGa_{1-x}N$ layer, the $In_xAl_{1-x}N$ layer and the $In_xAl_yGa_{1-x-y}N$ layer may include forming a source electrode and a drain electrode on the layer selected from the group consisting of the $Al_xGa_{1-x}N$ layer, the $In_xAl_{1-x}N$ layer and the $In_xAl_yGa_{1-x-y}N$ layer, and forming the sensing material layer on a portion of the region between the source electrode and the drain electrode.

Here, a GaN cap layer, an oxide film layer or a nitride film layer may be further formed in a single layer or multiple layers on the layer selected from the group consisting of the $Al_xGa_{1-x}N$ layer, the $In_xAl_{1-x}N$ layer and the $In_xAl_yGa_{1-x-y}N$ layer, and the thickness of the GaN cap layer, the oxide film layer or the nitride film layer may be 30 nm or less.

Here, the forming the sensing material layer on the layer selected from the group consisting of the $Al_xGa_{1-x}N$ layer, the $In_xAl_{1-x}N$ layer and the $In_xAl_yGa_{1-x-y}N$ layer may include forming an ohmic contact electrode on the layer selected from the group consisting of the $Al_xGa_{1-x}N$ layer, the $In_xAl_{1-x}N$ layer and the $In_xAl_yGa_{1-x-y}N$ layer, and forming the sensing material layer for Schottky contact formation and an ohmic contact electrode connected thereto.

Here, the heat generated by applying current to the n-type or p-type GaN layer may be transferred to the sensing material layer.

In the $Al_xGa_{1-x}N$ layer, x may satisfy $0<x\leq 1$, and in the $In_xAl_{1-x}N$ layer, x may satisfy $0<x\leq 1$.

In the $In_xAl_yGa_{1-x-y}N$ layer, x and y may satisfy $0<x\leq 1$, $0<y\leq 1$, $0<(x+y)\leq 1$.

In the $Al_xGa_{1-x}N$ layer for forming the barrier layer, x may satisfy $0<x\leq 1$, and in the $In_xAl_{1-x}N$ layer for forming the barrier layer, x may satisfy $0<x\leq 1$.

The method of the invention may further include separating the substrate from the n-type or p-type GaN layer.

Here, the substrate may be made of any one material selected from the group consisting of sapphire, AlN, diamond, BN, SiC, Si and GaN.

In addition, the present invention provides a gallium nitride-based sensor having a heater structure, comprising a substrate, an n-type or p-type GaN layer grown on the substrate, a GaN ($Al_xGa_{1-x}N$, $In_xAl_{1-x}N$, or high-resistance GaN)-based monolayered or multilayered barrier layer grown on the n-type or p-type GaN layer, a u-GaN layer grown on the barrier layer, a layer selected from the group consisting of an $Al_xGa_{1-x}N$ layer, an $In_xAl_{1-x}N$ layer and an $In_xAl_yGa_{1-x-y}N$ layer grown on the u-GaN layer, an electrode formed along a pattern formed on the n-type or p-type GaN layer, and a sensing material layer formed on the layer selected from the group consisting of the $Al_xGa_{1-x}N$ layer, the $In_xAl_{1-x}N$ layer and the $In_xAl_yGa_{1-x-y}N$ layer.

Here, the n-type or p-type GaN layer may function as a heater for generating heat due to the current applied to the electrode. Also, the threshold voltage of the sensor device may be adjusted by changing the applied voltage.

Here, the barrier layer may be provided in the form of any one layer or a combination of layers selected from among an $Al_xGa_{1-x}N$ layer, an $In_xAl_{1-x}N$ layer and a high-resistance GaN layer.

Here, the barrier layer may function to prevent the current flowing in the n-type or p-type GaN layer from flowing to the sensor structure on the barrier layer.

Here, the sensor of the invention may further include a source electrode and a drain electrode formed on the layer selected from the group consisting of the $Al_xGa_{1-x}N$ layer, the $In_xAl_{1-x}N$ layer and the $In_xAl_yGa_{1-x-y}N$ layer, and the sensing material layer may be formed on a portion of the region between the source electrode and the drain electrode.

Here, the sensor of the invention may further include an ohmic contact electrode, formed on the layer selected from the group consisting of the $Al_xGa_{1-x}N$ layer, the $In_xAl_{1-x}N$ layer and the $In_xAl_yGa_{1-x-y}N$ layer, and an ohmic contact electrode connected to the sensing material layer for Schottky contact formation.

In the $Al_xGa_{1-x}N$ layer, x may satisfy $0<x\leq 1$, and in the $In_xAl_{1-x}N$ layer, x may satisfy $0<x\leq 1$.

In the $In_xAl_yGa_{1-x-y}N$ layer, x and y may satisfy $0<x\leq 1$, $0<y\leq 1$, $0<(x+y)\leq 1$.

In the $Al_xGa_{1-x}N$ layer for forming the barrier layer, x may satisfy $0<x\leq 1$, and in the $In_xAl_{1-x}N$ layer for forming the barrier layer, x may satisfy $0<x\leq 1$.

Here, the heat generated by applying current to the n-type or p-type GaN layer may be transferred to the sensing material layer.

Here, the substrate may be made of any one material selected from the group consisting of sapphire, AlN, diamond, BN, SiC, Si and GaN.

Here, the n-type or p-type GaN layer formed on the substrate may be formed in a stripe shape, and the thickness, width, gap, and electrical conductivity of the stripe shape may be adjusted to thereby facilitate control of the reaction time (sensitivity) of the sensing material layer and the restoration time.

Here, the substrate may be separated from the n-type or p-type GaN layer and then transferred to a third substrate.

Here, the third substrate may be made of Si, Ge, W, Cr, Ni, Cu or alloys thereof, amorphous AlN, amorphous SiC, graphite, nanocarbon, or a polymer material.

Here, the polymer material may include any one selected from the group consisting of polycarbonate (PC), polyethylene naphthalate (PEN), polynorbornene, polyacrylate, polyvinyl alcohol, polyimide, polyethylene terephthalate (PET), polyethersulfone (PES), polystyrene (PS), polypropylene (PP), polyethylene (PE), polyvinylchloride (PVC), polyamide (PA), polybutylene terephthalate (PBT), polymethyl methacrylate (PMMA) and polydimethylsiloxane (PDMS).

According to the present invention pertaining to a gallium nitride-based sensor having a heater structure and a method of manufacturing the same, a HEMT sensor or a Schottky diode sensor can be heated using an n-GaN (or p-GaN) layer, thus increasing the sensitivity of the sensor and decreasing the restoration time. As such, the heater structure using the n-GaN (or p-GaN) layer is located directly below the sensor structure, thereby reducing power consumption and rapidly changing the temperature of the sensing material.

Also, an n-GaN (or p-GaN) epitaxial layer having high conductivity and a barrier layer usable as an insulator are grown on a heterogeneous substrate (sapphire, AlN, diamond, BN, Si, SiC, etc.), and then a HEMT structure, a Schottky diode structure, or the like is formed, thereby easily manufacturing the gallium nitride-based sensor having a heater structure.

DETAILED DESCRIPTION OF THE INVENTION

Figure 1A:
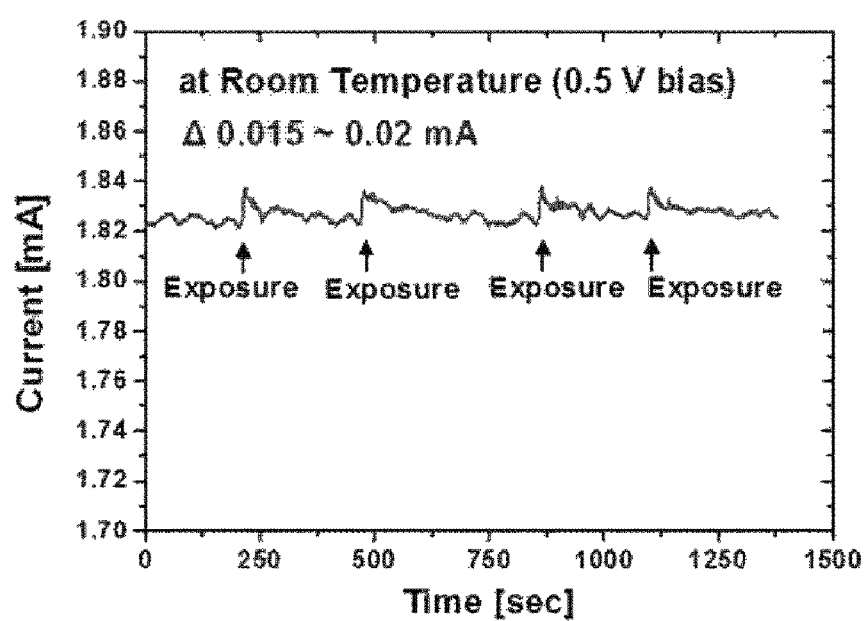
FIGS. 1A to 1C illustrate changes in sensitivity of a hydrogen sensor depending on the temperature.
Figure 1B:
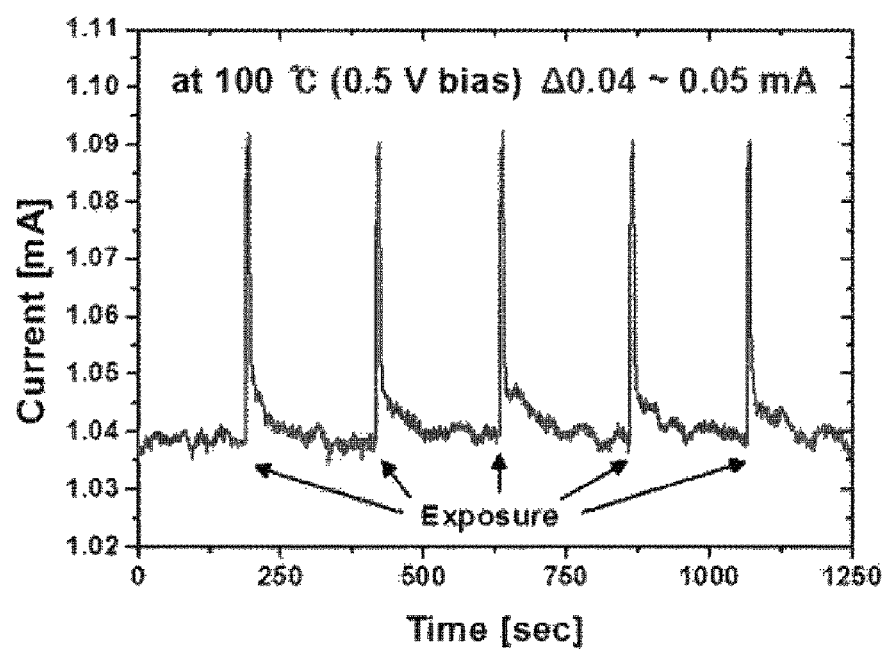
Figure 1C:
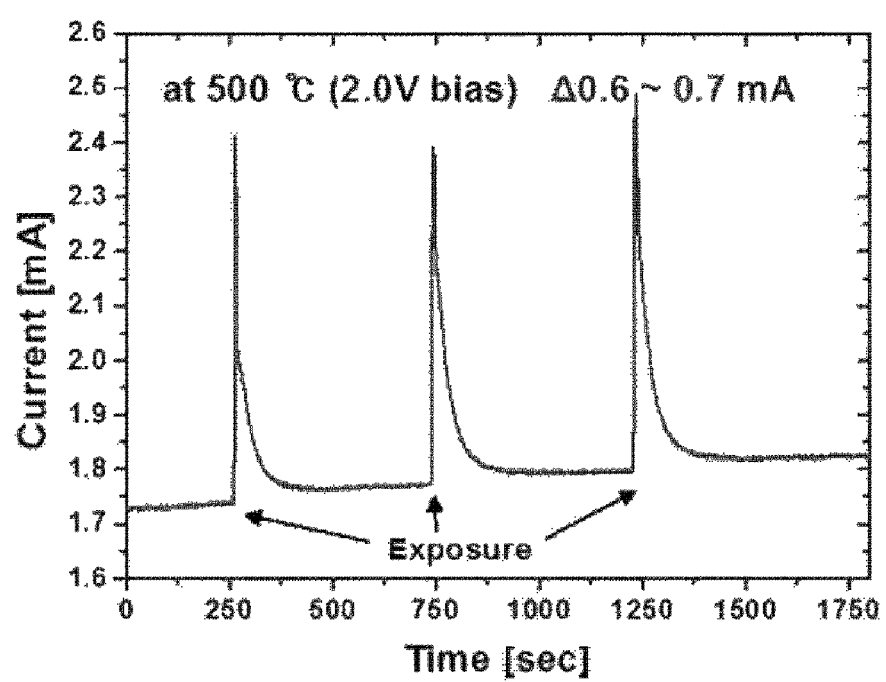

Reference will now be made in detail to various embodiments of the present invention, specific examples of which are illustrated in the accompanying drawings and described below, since the embodiments of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims. Throughout the drawings, the same reference numerals refer to the same or like elements.

It will be understood that, although the terms "first", "second", "A", "B", etc. may be used herein to describe various elements, these elements are not intended to be limited by these terms. These terms are only used to distinguish one element from another element. For instance, a first element discussed below could be termed a second element without departing from the teachings of the present invention. Similarly, the second element could also be termed the first element. As used herein, the term "and/or" may include any one of the listed items and any combination of one or more thereof.

It will be understood that when an element is referred to as being "coupled" or "connected" to another element, it can be directly coupled or connected to the other element, or intervening elements may be present therebetween. In contrast, it should be understood that when an element is referred to as being "directly coupled" or "directly connected" to another element, there are no intervening elements present.

The terminology used herein is for the purpose of describing particular embodiments only and is not intended to be limiting of the present invention. As used herein, the singular forms are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which the present invention belongs. It will be further understood that terms used herein should be interpreted as having a meaning that is consistent with their meaning in the context of this specification and the relevant art and are not to be interpreted in an idealized or overly formal sense unless expressly so defined herein.

Hereinafter, a detailed description will be given of preferred embodiments of the present invention with reference to the appended drawings.

Figure 2:
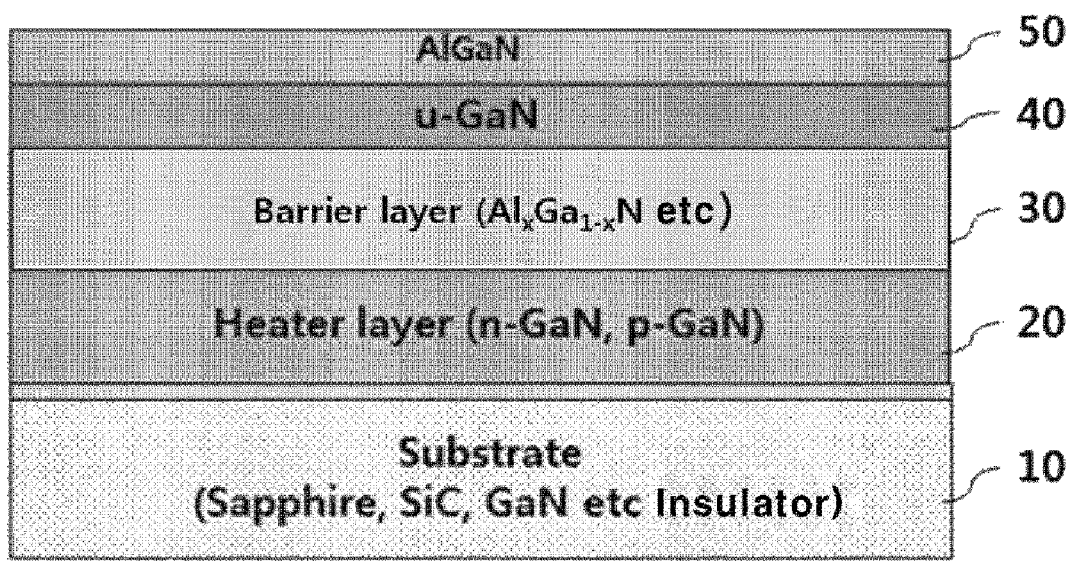
FIG. 2 illustrates the epitaxial thin film growth for manufacturing a gallium nitride-based sensor having a heater structure according to an embodiment of the present invention.

FIG. 2 illustrates the epitaxial thin film growth for manufacturing a gallium nitride-based sensor having a heater structure according to an embodiment of the present invention.

With reference to FIG. 2, the epitaxial thin film for manufacturing a gallium nitride-based sensor having a heater structure according to an embodiment of the present invention may be configured to include a substrate 10, an n-type or p-type GaN layer 20 grown on the substrate, a GaN ($Al_xGa_{1-x}N$, $In_xAl_{1-x}N$, or high-resistance GaN)-based monolayered or multilayered barrier layer 30 grown on the n-type or p-type GaN layer, a u-GaN layer 40 grown on the barrier layer 30, and a layer 50 selected from the group consisting of an $Al_xGa_{1-x}N$ layer, an $In_xAl_{1-x}N$ layer and an $In_xAl_yGa_{1-x-y}N$ layer, grown on the u-GaN layer. Herein, the substrate 10 may be made of any one material selected from the group consisting of sapphire, AlN, diamond, BN, SiC, Si and GaN.

In particular, the n-type or p-type GaN layer 20 may function as a heater for generating heat due to the current applied to an electrode. Specifically, since the barrier layer 30 is formed on the n-type or p-type GaN layer 20, when current is applied to the n-type or p-type GaN layer 20, the current flows in the transverse direction of the n-type or p-type GaN layer 20, thereby generating heat. Here, the barrier layer 30 may be provided in the form of any one layer or a combination of layers selected from among an $Al_xGa_{1-x}N$ layer, an $In_xAl_{1-x}N$ layer and a high-resistance GaN layer, and may function to prevent the current flowing in the n-type or p-type GaN layer 20 from flowing to the sensor structure on the barrier layer 30.

The n-type or p-type GaN layer 20 having high conductivity is interposed between the substrate 10 and the barrier layer 30, whereby epitaxial thin film growth may be performed.

Figure 3:
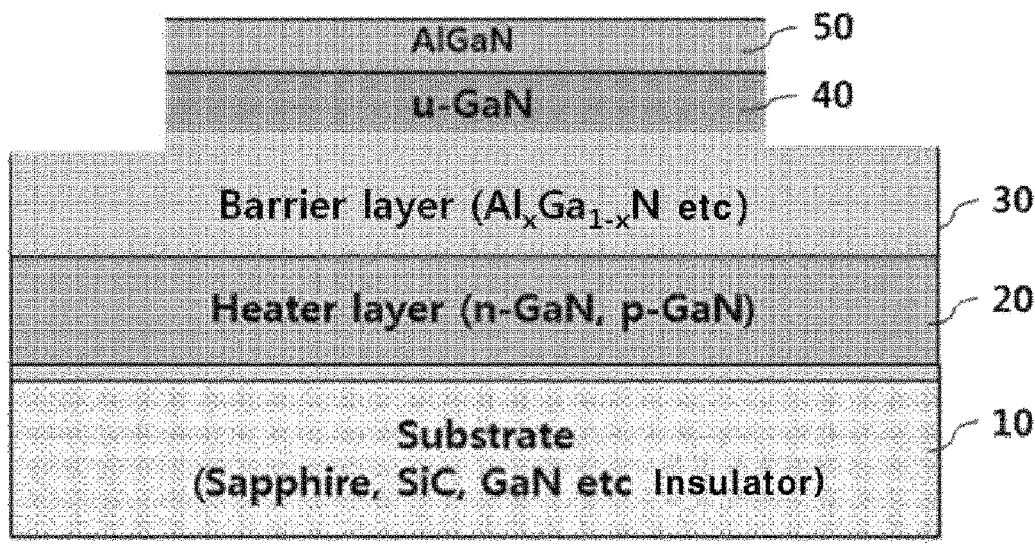
FIG. 3 illustrates the MESA isolation on the epitaxial thin film for manufacturing a gallium nitride-based sensor having a heater structure according to an embodiment of the present invention.
Figure 4:
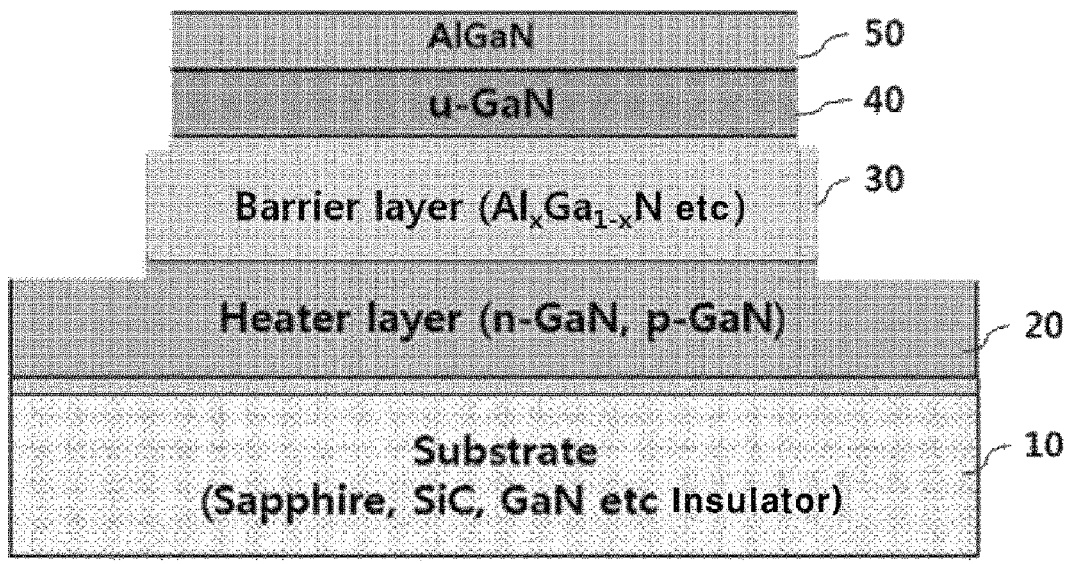
FIG. 4 illustrates the patterning for forming an electrode on the epitaxial thin film for manufacturing a gallium nitride-based sensor having a heater structure according to an embodiment of the present invention.
Figure 5:
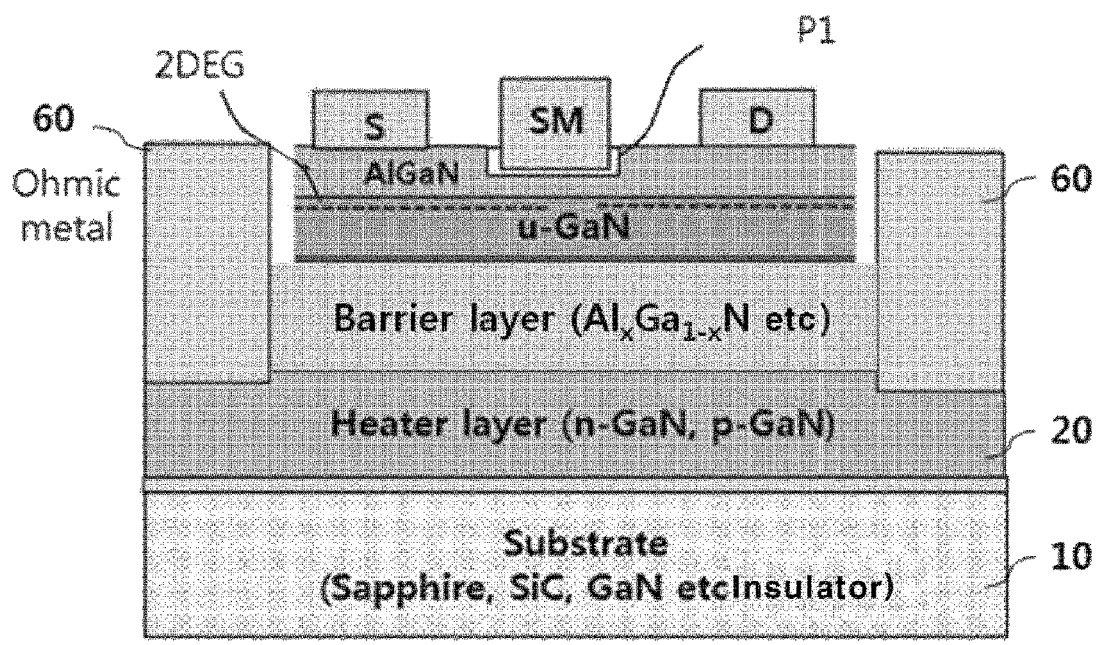
FIG. 5 illustrates the electrode formation and the HEMT formation for manufacturing a gallium nitride-based sensor having a heater structure according to an embodiment of the present invention.

FIG. 3 illustrates the MESA isolation on the epitaxial thin film for manufacturing a gallium nitride-based sensor having a heater structure according to an embodiment of the present invention, FIG. 4 illustrates the patterning for forming an electrode on the epitaxial thin film for manufacturing a gallium nitride-based sensor having a heater structure according to an embodiment of the present invention, and FIG. 5 illustrates the electrode formation and the HEMT formation for manufacturing a gallium nitride-based sensor having a heater structure according to an embodiment of the present invention.

With reference to FIGS. 2 to 5, the manufacture of a gallium nitride-based HEMT sensor having a heater structure is described below.

The epitaxial thin film as shown in FIG. 2, comprising the substrate 10, the n-type or p-type GaN layer 20, the barrier layer 30, the u-GaN layer 40 and the layer 50 selected from the group consisting of the $Al_xGa_{1-x}N$ layer, the $In_xAl_{1-x}N$ layer and the $In_xAl_yGa_{1-x-y}N$ layer, may be grown, and such a thin film structure is made structurally stable by continuously growing the GaN-based layers.

As necessary, a GaN cap layer, an oxide film layer or a nitride film layer may be further formed in a single layer or multiple layers on the layer selected from the group consisting of the $Al_xGa_{1-x}N$ layer, the $In_xAl_{1-x}N$ layer and the $In_xAl_yGa_{1-x-y}N$ layer. The GaN cap layer, the oxide film layer or the nitride film layer preferably has a thickness of 30 nm or less. For example, the thickness of the GaN cap layer, the oxide film layer or the nitride film layer may be 10 nm~30 nm.

With reference to FIG. 3, the MESA isolation may be performed on the thin film structure of FIG. 2 for manufacturing the gallium nitride-based sensor having a heater structure. Specifically, some outer portions of the layer 50 selected from the group consisting of the $Al_xGa_{1-x}N$ layer, the $In_xAl_{1-x}N$ layer and the $In_xAl_yGa_{1-x-y}N$ layer, the u-GaN layer 40, and the barrier layer 30 may be etched.

With reference to FIG. 4, the patterning for forming an electrode may be performed on the epitaxial thin film for manufacturing the gallium nitride-based sensor having a heater structure. Specifically, the n-type or p-type GaN layer 20 may be patterned so as to contact the electrode.

With reference to FIG. 5, the electrode 60 may be formed along the pattern formed on the n-type or p-type GaN layer 20.

Also, a source electrode S and a drain electrode D may be formed on the layer 50 selected from the group consisting of the $Al_xGa_{1-x}N$ layer, the $In_xAl_{1-x}N$ layer and the $In_xAl_yGa_{1-x-y}N$ layer, and a sensing material layer SM may be formed on a portion of the region between the source electrode S and the drain electrode D, thereby manufacturing a gallium nitride-based HEMT sensor. Here, the sensing material layer may be formed in a recess region P1 made by etching a portion of the layer 50 selected from the group consisting of the $Al_xGa_{1-x}N$ layer, the $In_xAl_{1-x}N$ layer and the $In_xAl_yGa_{1-x-y}N$ layer.

For example, the value x of the $Al_xGa_{1-x}N$ layer may satisfy $0<x\leq1$, the value x of the $In_xAl_{1-x}N$ layer may satisfy $0<x\leq1$, and the values x and y of the $In_xAl_yGa_{1-x-y}N$ layer may satisfy $0<x\leq1$, $0<y\leq1$, $0<(x+y)\leq1$.

The value x of the $Al_xGa_{1-x}N$ layer for forming the barrier layer 30 may satisfy $0<x\leq1$, and the value x of the $In_xAl_{1-x}N$ layer for forming the barrier layer 30 may satisfy $0<x\leq1$.

The n-type or p-type GaN layer 20 may function as a heater for generating heat due to current applied to the electrode 60. Thus, the gallium nitride-based HEMT sensor may be configured such that heat generated by applying current to the n-type or p-type GaN layer 20 may be rapidly transferred to the sensing material layer SM via the barrier layer, the u-GaN layer and the layer selected from the group consisting of the $Al_xGa_{1-x}N$ layer, the $In_xAl_{1-x}N$ layer and the $In_xAl_yGa_{1-x-y}N$ layer.

Figure 6:
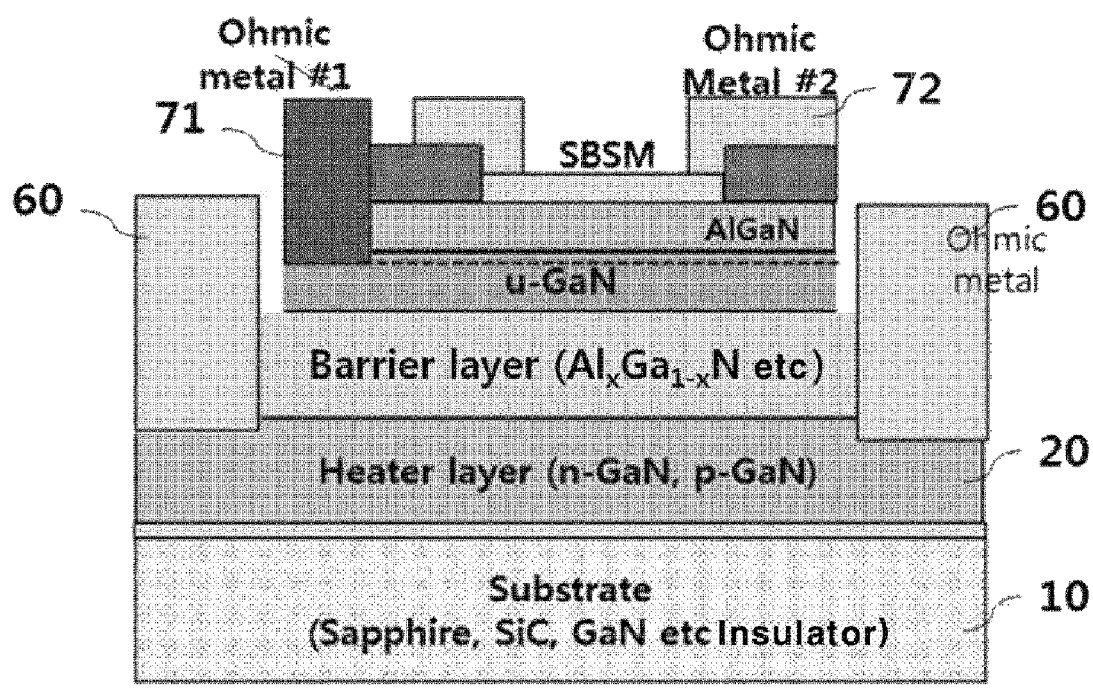
FIG. 6 illustrates the electrode formation and the Schottky diode formation for manufacturing a gallium nitride-based sensor having a heater structure according to an embodiment of the present invention.

FIG. 6 illustrates the electrode formation and the Schottky diode formation for manufacturing the gallium nitride-based sensor having a heater structure according to an embodiment of the present invention.

With reference to FIGS. 2 to 4 and FIG. 6, the manufacture of a gallium nitride-based Schottky diode sensor having a heater structure is described below.

The epitaxial thin film as shown in FIG. 2, comprising the substrate 10, the n-type or p-type GaN layer 20, the barrier layer 30, the u-GaN layer 40 and the layer 50 selected from the group consisting of the $Al_xGa_{1-x}N$ layer, the $In_xAl_{1-x}N$ layer and the $In_xAl_yGa_{1-x-y}N$ layer, may be grown, and such a thin film structure is made structurally stable by continuously growing the GaN-based layers.

With reference to FIG. 3, the MESA isolation may be performed on the thin film structure of FIG. 2 for manufacturing the gallium nitride-based sensor having a heater structure. Specifically, some outer portions of the layer 50 selected from the group consisting of the $Al_xGa_{1-x}N$ layer, the $In_xAl_{1-x}N$ layer and the $In_xAl_yGa_{1-x-y}N$ layer, the u-GaN layer 40, and the barrier layer 30 may be etched.

With reference to FIG. 4, the patterning for forming an electrode may be performed on the epitaxial thin film for manufacturing the gallium nitride-based sensor having a heater structure. Specifically, the n-type or p-type GaN layer 20 may be patterned so as to contact the electrode.

With reference to FIG. 6, the electrode 60 may be formed along the pattern formed on the n-type or p-type GaN layer 20.

Also, an ohmic contact electrode 71 may be formed on the layer 50 selected from the group consisting of the $Al_xGa_{1-x}N$ layer, the $In_xAl_{1-x}N$ layer and the $In_xAl_yGa_{1-x-y}N$ layer, and an ohmic contact electrode 72 that is connected to a sensing material layer (SBSM: Schottky Barrier Sensing Materials) for Schottky contact formation may be formed, thereby manufacturing a gallium nitride-based Schottky diode sensor.

The n-type or p-type GaN layer 20 may function as a heater for generating heat due to current applied to the electrode 60. Thus, the gallium nitride-based Schottky diode sensor may be configured such that heat generated by applying current to the n-type or p-type GaN layer 20 may be rapidly transferred to the sensing material layer (SBSM) via the barrier layer, the u-GaN layer and the layer selected from the group consisting of the $Al_xGa_{1-x}N$ layer, the $In_xAl_{1-x}N$ layer and the $In_xAl_yGa_{1-x-y}N$ layer.

Figure 7:
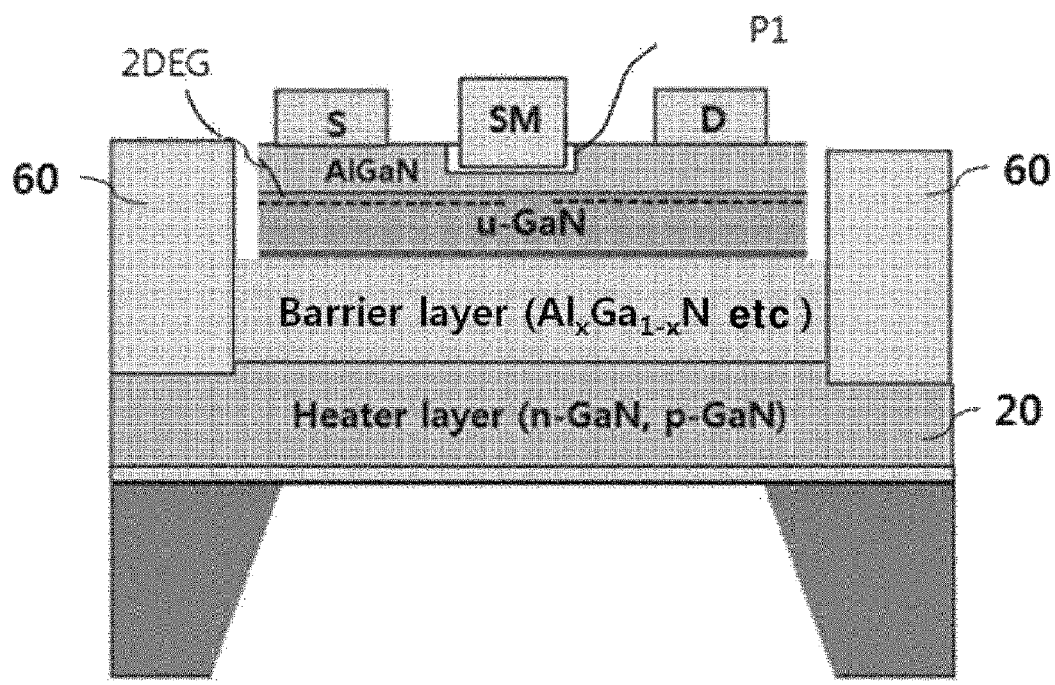
FIG. 7 illustrates the electrode formation and the membrane formation for manufacturing a gallium nitride-based sensor having a heater structure according to an embodiment of the present invention.

FIG. 7 illustrates the electrode formation and the membrane formation for manufacturing the gallium nitride-based sensor having a heater structure according to an embodiment of the present invention.

With reference to FIGS. 2 to 4 and FIG. 7, the manufacture of a gallium nitride-based membrane sensor having a heater structure is described below.

The epitaxial thin film as shown in FIG. 2, comprising the substrate 10, the n-type or p-type GaN layer 20, the barrier layer 30, the u-GaN layer 40 and the layer 50 selected from the group consisting of the $Al_xGa_{1-x}N$ layer, the $In_xAl_{1-x}N$ layer and the $In_xAl_yGa_{1-x-y}N$ layer, may be grown, and such a thin film structure is made structurally stable by continuously growing the GaN-based layers.

With reference to FIG. 3, the MESA isolation may be performed on the thin film structure of FIG. 2 for manufacturing the gallium nitride-based sensor having a heater structure. Specifically, some outer portions of the layer 50 selected from the group consisting of the $Al_xGa_{1-x}N$ layer, the $In_xAl_{1-x}N$ layer and the $In_xAl_yGa_{1-x-y}N$ layer, the u-GaN layer 40, and the barrier layer 30 may be etched.

With reference to FIG. 4, the patterning for forming an electrode may be carried out on the epitaxial thin film for manufacturing the gallium nitride-based sensor having a heater structure. Specifically, the n-type or p-type GaN layer 20 may be patterned so as to contact the electrode.

With reference to FIG. 7, the electrode 60 may be formed along the pattern formed on the n-type or p-type GaN layer 20.

Also, a source electrode S and a drain electrode D may be formed on the layer 50 selected from the group consisting of the $Al_xGa_{1-x}N$ layer, the $In_xAl_{1-x}N$ layer and the $In_xAl_yGa_{1-x-y}N$ layer, a sensing material layer SM may be formed on a portion of the region between the source electrode S and the drain electrode D, and the substrate 10 may be separated from the n-type or p-type GaN layer 20 and then transferred to a third substrate, thereby manufacturing a gallium nitride-based membrane or flexible sensor. Here, the sensing material layer may be formed in a recess region P1 made by etching a portion of the layer 50 selected from the group consisting of the $Al_xGa_{1-x}N$ layer, the $In_xAl_{1-x}N$ layer and the $In_xAl_yGa_{1-x-y}N$ layer.

Figure 8:
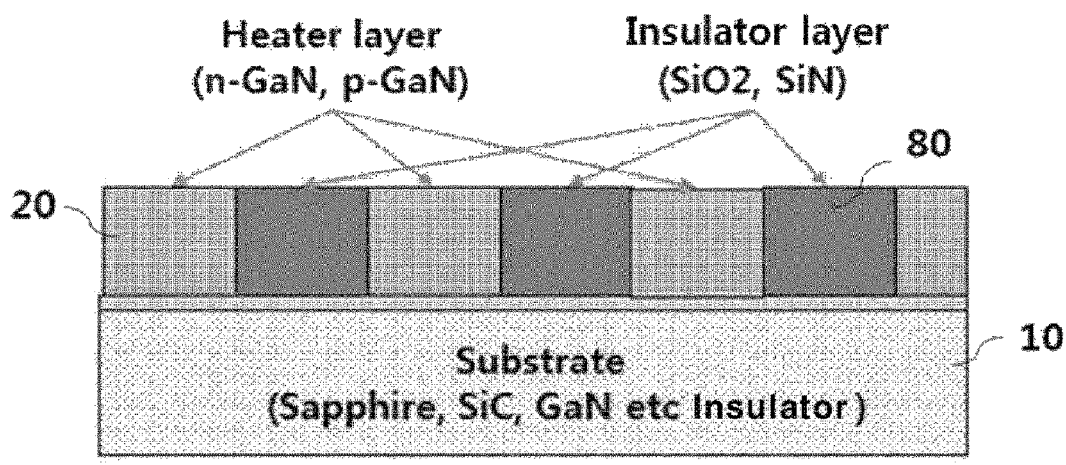
FIG. 8 illustrates the manufacture of a gallium nitride-based sensor having a heater structure according to another embodiment of the present invention.

FIG. 8 illustrates the manufacture of a gallium nitride-based sensor having a heater structure according to another embodiment of the present invention.

With reference to FIG. 8, an insulator layer 80 may be formed in a stripe shape on a substrate 10.

An n-type or p-type GaN layer 20 may be grown on the substrate 10 having the stripe-shaped insulator layer 80 formed thereon, and such an n-type or p-type GaN layer 20 may function as a heater. Specifically, the n-type or p-type GaN layer 20 may be grown in the stripe-shaped insulator layer 80 to thus have a stripe shape.

Accordingly, a sensor structure may be formed on the insulator layer 80 and the n-type or p-type GaN layer 20, having the stripe shape, thereby manufacturing a gallium nitride-based sensor having a heater structure.

The stripe-shaped n-type or p-type GaN layer 20 is adjusted in the thickness, width, gap, and electrical conductivity of the stripe shape, thus obtaining the gallium nitride-based sensor in which the temperature of the sensing material layer, power consumption, etc. may be easily controlled.

In order to easily separate the substrate upon the formation of the stripe-shaped insulator layer 80, a GaN-based buffer layer may be interposed between the insulator layer 80 and the substrate.

For example, the heater layer 20 may be patterned so as to have a planar structure or a one-dimensional linear structure.

Furthermore, the substrate is separated from the n-type or p-type GaN layer 20, and may be transferred to the third substrate, and the third substrate may be made of Si, Ge, W, Cr, Ni, Cu or alloys thereof, amorphous AlN, amorphous SiC, graphite, nanocarbon, or a polymer material.

The polymer material may include any one selected from the group consisting of polycarbonate (PC), polyethylene naphthalate (PEN), polynorbornene, polyacrylate, polyvinyl alcohol, polyimide, polyethylene terephthalate (PET), polyethersulfone (PES), polystyrene (PS), polypropylene (PP), polyethylene (PE), polyvinylchloride (PVC), polyamide (PA), polybutylene terephthalate (PBT), polymethyl methacrylate (PMMA) and polydimethylsiloxane (PDMS).

As described hereinbefore, the gallium nitride-based sensor having a heater structure may be configured such that a process of growing an epitaxial thin film having high conductivity is included during the gallium nitride-based epitaxial thin film growth, and thus a heater structure may be embedded.

Specifically, on a heterogeneous substrate (sapphire, AlN, diamond, BN, SiC, Si, etc.), an n-GaN (or p-GaN) epitaxial layer having high conductivity and a barrier layer usable as an insulator are grown, and then a HEMT structure, a Schottky diode structure, or the like is formed, thereby manufacturing the gallium nitride-based sensor having a heater structure.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of manufacturing a gallium nitride-based sensor having a heater structure, comprising:
    growing an n-type or p-type GaN layer on a substrate;
    growing a barrier layer on the n-type or p-type GaN layer;
    sequentially growing a u-GaN layer and a layer selected from the group consisting of an $Al_xGa_{1-x}N$ layer, an $In_xAl_{1-x}N$ layer and an $In_xAl_yGa_{1-x-y}N$ layer on the barrier layer;
    patterning the n-type or p-type GaN layer so as to form an electrode;
    forming the electrode along a pattern formed on the n-type or p-type GaN layer; and
    forming a sensing material layer on the layer selected from the group consisting of the $Al_xGa_{1-x}N$ layer, the $In_xAl_{1-x}N$ layer and the $In_xAl_yGa_{1-x-y}N$ layer.

2. The method of claim 1, wherein the n-type or p-type GaN layer functions as a heater for generating heat due to current applied to the electrode.

3. The method of claim 1, wherein the barrier layer is formed in any one layer or a combination of layers selected from among an $Al_xGa_{1-x}N$ layer, an $In_xAl_{1-x}N$ layer and a high-resistance GaN layer.

4. The method of claim 1, wherein the forming the sensing material layer on the layer selected from the group consisting of the $Al_xGa_{1-x}N$ layer, the $In_xAl_{1-x}N$ layer and the $In_xAl_yGa_{1-x-y}N$ layer comprises:
    forming a source electrode and a drain electrode on the layer selected from the group consisting of the $Al_xGa_{1-x}N$ layer, the $In_xAl_{1-x}N$ layer and the $In_xAl_yGa_{1-x-y}N$ layer, and
    forming the sensing material layer on a portion of a region between the source electrode and the drain electrode.

5. The method of claim 1, wherein a GaN cap layer, an oxide film layer or a nitride film layer, having a thickness of 30 nm or less, is further formed in a single layer or multiple layers on the layer selected from the group consisting of the $Al_xGa_{1-x}N$ layer, the $In_xAl_{1-x}N$ layer and the $In_xAl_yGa_{1-x-y}N$ layer.

6. The method of claim 1, wherein the forming the sensing material layer on the layer selected from the group consisting of the $Al_xGa_{1-x}N$ layer, the $In_xAl_{1-x}N$ layer and the $In_xAl_yGa_{1-x-y}N$ layer comprises:
    forming an ohmic contact electrode on the layer selected from the group consisting of the $Al_xGa_{1-x}N$ layer, the $In_xAl_{1-x}N$ layer and the $In_xAl_yGa_{1-x-y}N$ layer, and
    forming the sensing material layer for Schottky contact formation and an ohmic contact electrode connected thereto.

7. The method of claim 2, wherein heat generated by applying current to the n-type or p-type GaN layer is transferred to the sensing material layer.

8. The method of claim 1, wherein in the $Al_xGa_{1-x}N$ layer, x satisfies $0<x\leq1$, and in the $In_xAl_{1-x}N$ layer, x satisfies $0<x\leq1$.

9. The method of claim 1, wherein in the $In_xAl_yGa_{1-x-y}N$ layer, x and y satisfy $0<x\leq1$, $0<y\leq1$, $0<(x+y)\leq1$.

10. The method of claim 3, wherein in the $Al_xGa_{1-x}N$ layer for forming the barrier layer, x satisfies $0<x\le 1$, and in the $In_xAl_{1-x}N$ layer for forming the barrier layer, x satisfies $0<x\le 1$.

11. The method of claim 1, further comprising separating the substrate from the n-type or p-type GaN layer.

12. The method of claim 1, wherein the substrate is made of any one material selected from the group consisting of sapphire, AlN, diamond, BN, SiC, Si and GaN.

13. The method of claim 1, wherein the n-type or p-type GaN layer formed on the substrate is provided in a stripe shape, and a thickness, a width, a gap and electrical conductivity of the stripe shape are adjusted to thereby facilitate control of a reaction time (sensitivity) of the sensing material layer and a restoration time.

14. A gallium nitride-based sensor having a heater structure, comprising:
a substrate;
an n-type or p-type GaN layer grown on the substrate;
a barrier layer grown on the n-type or p-type GaN layer;
a u-GaN layer grown on the barrier layer;
a layer selected from the group consisting of an $Al_xGa_{1-x}N$ layer, an $In_xAl_{1-x}N$ layer and an $In_xAl_yGa_{1-x-y}N$ layer grown on the u-GaN layer;
an electrode formed along a pattern formed on the n-type or p-type GaN layer; and
a sensing material layer formed on the layer selected from the group consisting of the $Al_xGa_{1-x}N$ layer, the $In_xAl_{1-x}N$ layer and the $In_xAl_yGa_{1-x-y}N$ layer.

15. The gallium nitride-based sensor of claim 14, wherein the n-type or p-type GaN layer functions as a heater for generating heat due to current applied to the electrode.

16. The gallium nitride-based sensor of claim 14, wherein the barrier layer is formed in any one layer or a combination of layers selected from among an $Al_xGa_{1-x}N$ layer, an $In_xAl_{1-x}N$ layer and a high-resistance GaN layer.

17. The gallium nitride-based sensor of claim 14, further comprising a source electrode and a drain electrode formed on the layer selected from the group consisting of the $Al_xGa_{1-x}N$ layer, the $In_xAl_{1-x}N$ layer and the $In_xAl_yGa_{1-x-y}N$ layer, the sensing material layer being formed on a portion of a region between the source electrode and the drain electrode.

18. The gallium nitride-based sensor of claim 14, further comprising a GaN cap layer, an oxide film layer or a nitride film layer, configured to have a thickness of 30 nm or less and formed in a single layer or multiple layers on the layer selected from the group consisting of the $Al_xGa_{1-x}N$ layer, the $In_xAl_{1-x}N$ layer and the $In_xAl_yGa_{1-x-y}N$ layer.

19. The gallium nitride-based sensor of claim 14, further comprising:
an ohmic contact electrode formed on the layer selected from the group consisting of the $Al_xGa_{1-x}N$ layer, the $In_xAl_{1-x}N$ layer and the $In_xAl_yGa_{1-x-y}N$ layer; and
an ohmic contact electrode connected to the sensing material layer for Schottky contact formation.

20. The gallium nitride-based sensor of claim 14, wherein in the $Al_xGa_{1-x}N$ layer, x satisfies $0<x\le 1$, and in the $In_xAl_{1-x}N$ layer, x satisfies $0<x\le 1$.

21. The gallium nitride-based sensor of claim 14, wherein in the $In_xAl_yGa_{1-x-y}N$ layer, x and y satisfy $0<x\le 1$, $0<y\le 1$, and $0<(x+y)\le 1$.

22. The gallium nitride-based sensor of claim 16, wherein in the $Al_xGa_{1-x}N$ layer for forming the barrier layer, x satisfies $0<x\le 1$, and in the $In_xAl_{1-x}N$ layer for forming the barrier layer, x satisfies $0<x\le 1$.

23. The gallium nitride-based sensor of claim 14, wherein heat generated by applying current to the n-type or p-type GaN layer is transferred to the sensing material layer.

24. The gallium nitride-based sensor of claim 14, wherein the substrate is made of any one material selected from the group consisting of sapphire, AlN, diamond, BN, SiC, Si and GaN.

25. The gallium nitride-based sensor of claim 14, wherein the n-type or p-type GaN layer formed on the substrate is provided in a stripe shape, and a thickness, a width, a gap and electrical conductivity of the stripe shape are adjusted to thereby facilitate control of a reaction time (sensitivity) of the sensing material layer and a restoration time.

* * * * *